US009938242B2

United States Patent
Ueda et al.

(10) Patent No.: US 9,938,242 B2
(45) Date of Patent: Apr. 10, 2018

(54) METHODS FOR PRODUCING OPTICALLY ACTIVE VALERIC ACID DERIVATIVES

(71) Applicant: DAIICHI SANKYO COMPANY, LIMITED, Tokyo (JP)

(72) Inventors: Tsuyoshi Ueda, Kanagawa (JP); Kazutoshi Ukai, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 15/512,471

(22) PCT Filed: Sep. 17, 2015

(86) PCT No.: PCT/JP2015/076391
§ 371 (c)(1),
(2) Date: Mar. 17, 2017

(87) PCT Pub. No.: WO2016/043254
PCT Pub. Date: Mar. 24, 2016

(65) Prior Publication Data
US 2017/0291878 A1    Oct. 12, 2017

(30) Foreign Application Priority Data
Sep. 18, 2014   (JP) ................ 2014-189572

(51) Int. Cl.
C07D 233/64    (2006.01)
A61K 31/417    (2006.01)
C07B 61/00    (2006.01)
C07B 53/00    (2006.01)

(52) U.S. Cl.
CPC .......... C07D 233/64 (2013.01); *A61K 31/417* (2013.01); *C07B 53/00* (2013.01); *C07B 61/00* (2013.01); *C07B 2200/07* (2013.01); *Y02P 20/55* (2015.11)

(58) Field of Classification Search
CPC .............................. C07D 233/64; C07B 53/00
See application file for complete search history.

(56) References Cited

U.S. PATENT DOCUMENTS

2013/0022587 A1*    1/2013   Nagata et al. ............... 424/94.1

FOREIGN PATENT DOCUMENTS

| | | |
|---|---|---|
| JP | 2007-537256 A | 12/2007 |
| JP | 2008-505903 A | 2/2008 |
| WO | 2001/094334 A1 | 12/2001 |
| WO | 2005/118529 A2 | 12/2005 |
| WO | 2006/017045 A2 | 2/2006 |

OTHER PUBLICATIONS

Appleby, Organic Letters, 2005, vol. 7, No. 10, p. 1931-1934.*
Lennon, Process Aspects of Asymmetric Hydrogenation, SCI Process Development Symposium, Dec. 5-7, 2007, p. 1-60.*
English Translation of International Search Report dated Dec. 22, 2015, in PCT Application No. PCT/JP2015/076391, 2 pages.
English Translation of Written Opinion dated Dec. 22, 2015, in PCT Application No. PCT/JP2015/076391, 6 pages.

* cited by examiner

*Primary Examiner* — Rebecca L Anderson
*Assistant Examiner* — Karen Cheng
(74) *Attorney, Agent, or Firm* — Dorsey & Whitney LLP

(57) ABSTRACT

A method for producing a compound (3), which comprises allowing a compound (1) to react with hydrogen gas in an inert solvent, in the presence of a specific chiral ligand and a ruthenium catalyst, or in the presence of an asymmetric transition metal complex catalyst previously generated from the chiral ligand and the ruthenium catalyst.

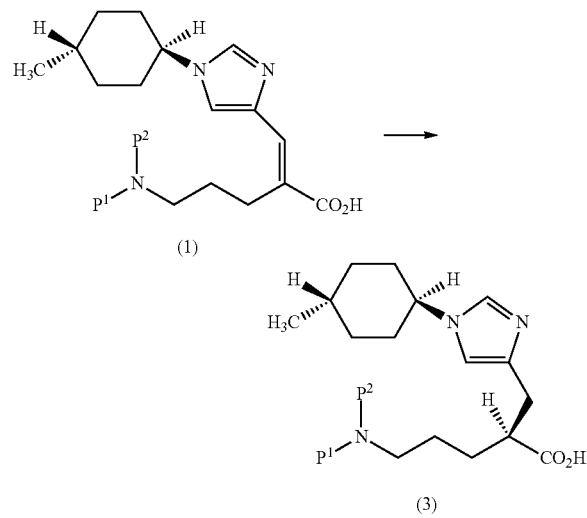

11 Claims, No Drawings

METHODS FOR PRODUCING OPTICALLY ACTIVE VALERIC ACID DERIVATIVES

This application is a national stage application under 35 U.S.C. § 371 of International Application No. PCT/JP2015/076391, filed Sep. 17, 2015, entitled "METHOD FOR PRODUCING OPTICALLY ACTIVE VALERIC ACID DERIVATIVE," which claims priority to Japanese Patent Application No. 2014-189572, filed Sep. 18, 2014.

TECHNICAL FIELD

The present invention relates to a novel method for producing an optically active valeric acid derivative substituted with a cycloalkyl group, which has an excellent TAFIa inhibitory activity.

BACKGROUND ART

Example 15 of Patent Literature 1 describes (2S)-5-amino-2-{[1-(trans-4-methylcyclohexyl)-1H-imidazol-4-yl]methyl}valeric acid having an excellent TAFIa enzyme inhibitory activity and a method for producing the same.

Specifically, ethyl 1-(trans-4-methylcyclohexyl)-1H-imidazole-4-carboxylate is used as a starting material, and reduction of an ester to an alcohol, oxidation of the alcohol to an aldehyde, Knoevenagel condensation and olefin reduction are performed to synthesize a racemate, methyl 5-[(tert-butoxycarbonyl)amino]-2-{[1-(trans-4-methylcyclohexyl)-1H-imidazol-4-yl]methyl}valerate. Thereafter, an enantiomer is separated from the compound using optically active column chromatography, the ester thereof is then hydrolyzed, and the protective group for the amino group is then removed, so as to produce an optically active form, (2S)-5-amino-2-{[1-(trans-4-methylcyclohexyl)-1H-imidazol-4-yl]methyl}valeric acid.

However, in the method of separating the racemate using optically active column chromatography, the enantiomer having a steric structure opposite to that intended is wasted, and such separation operations are complicated. Thus, this method is not industrially preferable.

CITATION LIST

Patent Literature

Patent Literature 1: International Publication No. WO 2011/115064

SUMMARY OF INVENTION

Technical Problem

The present inventors have conducted various studies directed towards solving the aforementioned problems. As a result, the inventors have discovered a production method, which is efficient and has simple operations, by adopting asymmetric reduction of olefins using a specific asymmetric transition metal complex catalyst, thereby completing the present invention.

Solution to Problem

The present invention includes the following [1] to [11].

[1] A method for producing a compound represented by the following formula (3):

[Formula 3]

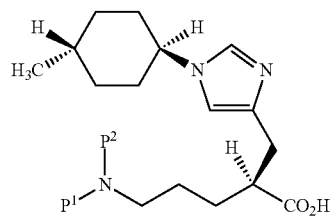

(3)

wherein $P^1$ and $P^2$ each independently represent a hydrogen atom or a protective group for the amino group,
wherein the method comprises allowing a compound represented by the following formula (1):

[Formula 1]

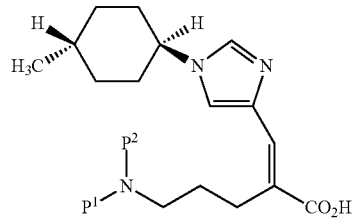

(1)

(wherein $P^1$ and $P^2$ are as defined above),
to react with hydrogen gas, in an inert solvent, in the presence of a chiral ligand represented by the following formula (2):

[Formula 2]

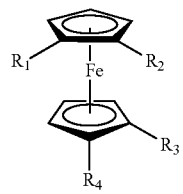

(2)

(wherein $R^1$ represents an (S)-ethyl-di-2-methylphenylphosphino group or an (S)-α-N,N-dimethylaminophenylmethyl group, $R^2$ represents a di-tert-butylphosphino group, a di(3,5-dimethyl-4-methoxyphenyl)-phosphino group, or a di(3,5-dimethylphenyl)-phosphino group, $R^3$ represents an (S)-α-N,N-dimethylaminophenylmethyl group or a hydrogen atom, and $R^4$ represents a di(3,5-dimethyl-4-methoxyphenyl)-phosphino group, a di(3,5-dimethylphenyl)-phosphino group, or a hydrogen atom), and a ruthenium catalyst, or in the presence of an asymmetric transition metal complex catalyst previously generated from the chiral ligand and the ruthenium catalyst.

[2] The production method according to the above [1], wherein at least one of $P^1$ and $P^2$ is a tert-butoxycarbonyl group, a methoxycarbonyl group, an ethoxycarbonyl group, a 2,2,2-trichloroethoxycarbonyl group, a 2-trimethylsilylethoxycarbonyl group, an allyloxycarbonyl group, a benzyloxycarbonyl group, a 4-methoxybenzyloxycarbonyl group, a 4-nitrobenzyloxycarbonyl group, a 2-nitrobenzyloxycarbonyl group, a 9-fluorenylmethyloxycarbonyl group, a benzyl group, a 4-methoxybenzyl group, a 2,3-dimethoxybenzyl group, a 3,4-dimethoxybenzyl group, a diphenylmethyl group, a triphenylmethyl group, a formyl group, an acetyl group, a trimethylacetyl group, a trichloroacetyl group, a trifluoroacetyl group, a benzoyl group, a benzenesulfonyl group, a p-toluenesulfonyl group, a 2-nitrobenzenesulfonyl group, a 4-nitrobenzenesulfonyl group, or a 2,4-dinitrobenzenesulfonyl group.

[3] The production method according to the above [1], wherein at least one of $P^1$ and $P^2$ is a tert-butoxycarbonyl group.

[4] The production method according to the above [1] to [4], wherein one of $P^1$ and $P^2$ is a tert-butoxycarbonyl group and the other is a hydrogen atom.

[5] The production method according to any one of the above [1] to [4], wherein the chiral ligand is (S)-1-[(R)-2-(di-tert-butylphosphino)ferrocenyl]-ethyl-di-2-methylphenylphosphine, (αS,αS)-2,2'-bis(α-N,N-dimethylaminophenylmethyl)-(R,R)-1,1'-bis[di-(3,5-dimethyl-4-methoxyphenyl)-phosphino]-ferrocene, or (αS,αS)-2,2'-bis(α-N,N-dimethylaminophenylmethyl)-(R,R)-1,1'-bis[di-(3,5-dimethylphenyl)phosphino]-ferrocene.

[6] The production method according to any one of the above [1] to [4], wherein the chiral ligand and the ruthenium catalyst are (S)-1-[(R)-2-(di-tert-butylphosphino)ferrocenyl]-ethyl-di-2-methylphenylphosphine and [RuCl$_2$(benzene)]$_2$, (αs,αs)-2,2'-bis(α-N,N-dimethylaminophenylmethyl)-(R,R)-1,1'-bis[di-(3,5-dimethyl-4-methoxyphenyl)-phosphino]-ferrocene and [RuCl$_2$(benzene)]$_2$, or (αS,αS)-2,2'-bis(α-N,N-dimethylaminophenylmethyl)-(R,R)-1,1'-bis[di-(3,5-dimethylphenyl)phosphino]-ferrocene and [RuCl$_2$(benzene)]$_2$.

[7] The production method according to any one of the above [1] to [4], wherein the chiral ligand and the ruthenium catalyst are (S)-1-[(R)-2-(di-tert-butylphosphino)ferrocenyl]-ethyl-di-2-methylphenylphosphine and [RuCl$_2$(benzene)]$_2$.

[8] The production method according to any one of the above [1] to [7], wherein the inert solvent is an alcohol.

[9] The production method according to any one of the above [1] to [7], wherein the inert solvent is methanol.

[10] A method for producing a compound represented by the following formula (4) or a pharmacologically acceptable salt thereof:

[Formula 4]

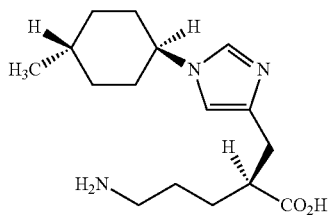

(4)

wherein the method comprises producing the compound represented by the formula (3) in accordance with the production method according to any one of the above [1] to [9], and then performing on the compound represented by the formula (3) a step of deprotecting the protective group(s) for the amino group.

[11] A method for producing a compound represented by the following formula (4) or a pharmacologically acceptable salt thereof:

[Formula 5]

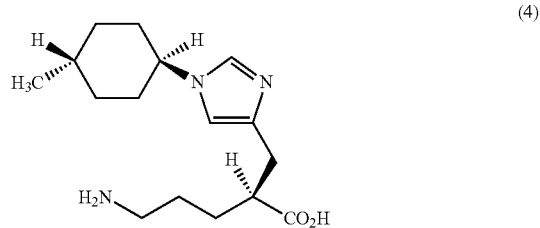

(4)

wherein the method comprises producing the compound represented by the formula (3) in accordance with the production method according to any one of claims 1 to 9, and then performing on the compound represented by the formula (3) the following steps (a) to (c):
(a) a step of adding (S)-2-amino-1-propanol to crystallize a salt of the compound, then,
(b) a step of adding an acid to remove the salt from the compound, and then,
(c) a step of deprotecting the protective group(s) for the amino group.

Advantageous Effects of Invention

According to the present invention, an optically active valeric acid derivative substituted with a cycloalkyl group, which has an excellent TAFIa inhibitory activity, can be efficiently produced by simple operations.

DESCRIPTION OF EMBODIMENTS

Hereinafter, the substituents used in the present description will be described.

A "protective group for the amino group" means a protective group generally used as a protective group for amino groups in the synthesis of organic compounds. Examples thereof include: alkoxycarbonyl groups such as a tert-butoxycarbonyl group, a methoxycarbonyl group, an ethoxycarbonyl group, a 2,2,2-trichloroethoxycarbonyl group, and 2-trimethylsilylethoxycarbonyl group; allyloxycarbonyl groups; arylmethoxycarbonyl groups such as a benzyloxycarbonyl group, a 4-methoxybenzyloxycarbonyl group, a 4-nitrobenzyloxycarbonyl group, and a 2-nitrobenzyloxycarbonyl group; 9-fluorenylmethyloxycarbonyl groups; arylmethyl groups such as a benzyl group, a 4-methoxybenzyl group, a 2,3-dimethoxybenzyl group, a 3,4-dimethoxybenzyl group, a diphenylmethyl group, and a triphenylmethyl group; alkanoyl groups such as a formyl group, an acetyl group, a trimethylacetyl group, a trichloroacetyl group, and a trifluoroacetyl group; aroyl groups such as a benzoyl group; and arylsulfonyl groups such as a benzenesulfonyl group, a p-toluenesulfonyl group, a 2-nitrobenzenesulfonyl group, a 4-nitrobenzenesulfonyl group, and a 2,4-dinitrobenzenesulfonyl group. These protective groups for amino groups may be selected according to, for example, the properties of the compound whose amino group is to be protected, and for removal of those protective groups as well, reagents and conditions may be selected according to the protective groups.

A "protective group for the carboxy group" means a protective group generally used as a protective group for carboxy groups in the synthesis of organic compounds. Examples thereof include alkyl groups such as a $C_1$-$C_8$ alkyl group, aryl groups such as a phenyl group, and arylalkyl groups such as a benzyl group. These protective groups for carboxy groups may be selected according to, for example, the properties of the compound whose carboxy group is to be protected, and for removal of those protective groups as well, reagents and conditions may be selected according to the protective groups.

Examples of references on the protection/deprotection of the carboxy and amino groups can include Peter G. M. Wuts, Theodora W. Greene, Greene's Protective Groups in Organic Synthesis 4th Edition (2007), Wiley-Interscience.

A "$C_1$-$C_8$ alkyl group" means a linear or branched saturated hydrocarbon group having 1 to 8 carbon atoms, and preferably, a linear or branched saturated hydrocarbon group having 1 to 4 carbon atoms ($C_1$-$C_4$ alkyl group). Examples thereof include a methyl group, an ethyl group, a propyl group, an isopropyl group, an n-butyl group, a sec-butyl group, a tert-butyl group, and an isobutyl group.

The production method of the present invention can be carried out in accordance with the following Method A.

Method A group, an ethoxycarbonyl group, a 2,2,2-trichloroethoxycarbonyl group, a 2-trimethylsilylethoxycarbonyl group, an allyloxycarbonyl group, a benzyloxycarbonyl group, a 4-methoxybenzyloxycarbonyl group, a 4-nitrobenzyloxycarbonyl group, a 2-nitrobenzyloxycarbonyl group, a 9-fluorenylmethyloxycarbonyl group, a benzyl group, a 4-methoxybenzyl group, a 2,3-dimethoxybenzyl group, a 3,4-dimethoxybenzyl group, a diphenylmethyl group, a triphenylmethyl group, a formyl group, an acetyl group, a trimethylacetyl group, a trichloroacetyl group, a trifluoroacetyl group, a benzoyl group, a benzenesulfonyl group, a p-toluenesulfonyl group, a 2-nitrobenzenesulfonyl group, a 4-nitrobenzenesulfonyl group, or a 2,4-dinitrobenzenesulfonyl group; more preferably, at least one of $P^1$ and $P^2$ represents a tert-butoxycarbonyl group; and further preferably, one of $P^1$ and $P^2$ is a tert-butoxycarbonyl group and the other is a hydrogen atom.

Step A1

The present step is a step of deprotecting the carboxy group of a compound (6) (which can be produced by the method described in the Examples, the method described in International Publication No. WO 2011/115064, or a method equivalent thereto) in an inert solvent, so as to produce a compound (1). Conditions for the deprotection are not particularly limited, as long as they are conditions generally

[Formula 6]

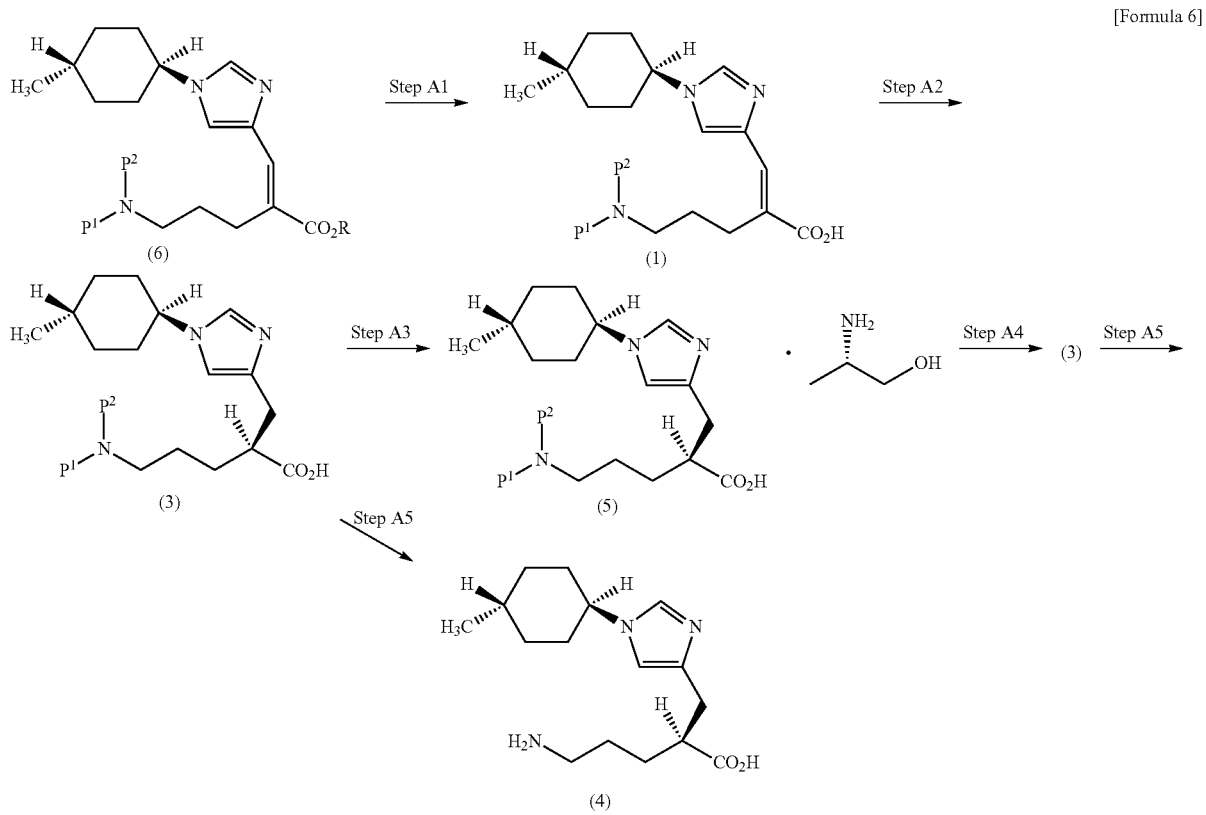

wherein R represents a protective group for the carboxy group, preferably a $C_1$-$C_8$ alkyl group, a benzyl group or a phenyl group, more preferably a $C_1$-$C_4$ alkyl group, and further preferably a methyl group. $P^1$ and $P^2$ each independently represent a hydrogen atom or a protective group for the amino group; preferably, at least one of $P^1$ and $P^2$ represents a tert-butoxycarbonyl group, a methoxycarbonyl used in the deprotection of protective groups for carboxy groups. For example, when the protective group for the carboxy group is a methyl group, deprotection is carried out by adding a base to the protective group in an inert solvent, and then hydrolyzing it.

The inert solvent used in the present step is generally water, or a mixture of water and an organic solvent. The organic solvent is not particularly limited, as long as it does not inhibit the reaction. Examples of the organic solvent include: nitrile solvents such as acetonitrile; ether solvents such as diethyl ether, 1,2-dimethoxyethane, and tetrahydrofuran; saturated hydrocarbon solvents such as hexane and pentane; aromatic hydrocarbon solvents such as benzene, toluene, and chlorobenzene; ketone solvents such as acetone and 2-butanone; amide solvents such as N,N-dimethylformamide, N,N-dimethylacetamide, and 1-methyl-2-pyrrolidone; alcohol solvents such as methanol and ethanol; and sulfoxide solvents such as dimethyl sulfoxide. The organic solvent is preferably a mixture of an alcohol solvent and water, or a mixture of an ether solvent and water, and more preferably a mixture of methanol and water, or a mixture of tetrahydrofuran and water.

Examples of the base used in the present step generally include: hydroxides of alkali metals, such as sodium hydroxide, potassium hydroxide, and lithium hydroxide; hydroxides of alkaline-earth metals, such as calcium hydroxide and barium hydroxide; and carbonates of alkali metals, such as sodium carbonate and potassium carbonate. Preferred examples include hydroxides of alkali metals, and a more preferred example is sodium hydroxide.

The base is used in the present step in an amount of generally 1 to 20 equivalents, preferably 2 to 10 equivalents, and more preferably 3 to 5 equivalents, with respect to the compound (4).

The reaction temperature applied in the present step is generally 0° C. to 80° C., preferably 10° C. to 50° C., and more preferably 15° C. to 30° C.

The reaction time applied in the present step is generally 1 hour to 72 hours, preferably 10 hours to 48 hours, and more preferably 15 hours to 30 hours.

Step A2

The present step is a step of allowing the compound (1) to react with hydrogen gas, in an inert solvent, in the presence of a chiral ligand and a ruthenium catalyst, or in the presence of a catalyst previously generated from the chiral ligand and the ruthenium catalyst, so as to produce a compound (3) having a high optical purity. When $P^1$ and $P^2$ are hydrogen atoms, a compound (4) or a pharmacologically acceptable salt thereof can be directly produced.

The inert solvent used in the present step is not particularly limited, as long as it does not inhibit the reaction. Examples of the inert solvent include: nitrile solvents such as acetonitrile; ether solvents such as diethyl ether, 1,2-dimethoxyethane, and tetrahydrofuran; saturated hydrocarbon solvents such as hexane and pentane; aromatic hydrocarbon solvents such as benzene, toluene, and chlorobenzene; ketone solvents such as acetone and 2-butanone; amide solvents such as N,N-dimethylformamide, N,N-dimethylacetamide, and 1-methyl-2-pyrrolidone; alcohol solvents such as methanol and ethanol; sulfoxide solvents such as dimethyl sulfoxide; ester solvents such as ethyl acetate; water; and mixed solvents thereof. The inert solvent is preferably alcohol, and more preferably methanol.

In the present step, a chiral ligand and a ruthenium catalyst can be used, and those may form a complex in the reaction system during the present step. Alternatively, a complex may have been formed from said chiral ligand and ruthenium catalyst before the present step, and the thus formed complex may be used as an asymmetric transition metal complex catalyst.

The chiral ligand used in the present step is preferably (S)-1-[(R)-2-(di-tert-butylphosphino)ferrocenyl]-ethyl-di-2-methylphenylphosphine, (αS,αS)-2,2'-bis(α-N,N-dimethyl-aminophenylmethyl)-(R,R)-1,1'-bis[di-(3,5-dimethyl-4-methoxyphenyl)-phosphino]-ferrocene, or (αS,αS)-2,2'-bis(α-N,N-dimethylaminophenylmethyl)-(R,R)-1,1'-bis[di-(3,5-dimethylphenyl)phosphino]-ferrocene. The ruthenium catalyst used in the present step is preferably [RuCl$_2$(benzene)]$_2$.

A combination of the chiral ligand and the ruthenium catalyst used in the present step is preferably a combination of (S)-1-[(R)-2-(di-tert-butylphosphino)ferrocenyl]-ethyl-di-2-methylphenylphosphine and [RuCl$_2$(benzene)]$_2$, a combination of (αS,αS)-2,2'-bis(α-N,N-dimethylaminophenylmethyl)-(R,R)-1,1'-bis[di-(3,5-dimethyl-4-methoxyphenyl)-phosphino]-ferrocene and [RuCl$_2$(benzene)]$_2$, or a combination of (αS,αS)-2,2'-bis(α-N,N-dimethylaminophenylmethyl)-(R,R)-1,1'-bis[di-(3,5-dimethylphenyl)phosphino]-ferrocene and [RuCl$_2$(benzene)]$_2$, and is more preferably a combination of (S)-1-[(R)-2-(di-tert-butylphosphino)ferrocenyl]-ethyl-di-2-methylphenylphosphine and [RuCl$_2$(benzene)]$_2$.

The chiral ligand is used in the present step in an amount of generally 0.1 mol % to 20 mol %, preferably 0.5 mol % to 10 mol %, and more preferably 1 mol % to 5 mol %, with respect to the compound (1).

The ruthenium catalyst is used in the present step in an amount of generally 0.1 mol % to 20 mol %, preferably 0.5 mol % to 10 mol %, and more preferably 1 mol % to 5 mol %, with respect to the compound (1).

The pressure of the hydrogen gas used in the present step is generally 1 to 1000 kPa, preferably 100 to 900 kPa, and more preferably 300 to 800 kPa.

The reaction temperature applied in the present step is generally 0° C. to 200° C., preferably 20° C. to 150° C., and more preferably 40° C. to 100° C.

The reaction time applied in the present step is generally 1 hour to 120 hours, preferably 3 hours to 72 hours, and more preferably 12 hours to 48 hours.

Step A3

The present step is a step of adding (S)-2-amino-1-propanol to the compound (3) in an inert solvent to crystallize a salt of the compound, so as to produce the salt (5) of the compound. By performing the present step and Step A4, the optical purities of the compound (3) and the compound (4) can be further improved.

The inert solvent used in the present step is not particularly limited, as long as it does not generally inhibit salt formation, and both a single solvent and a mixed solvent consisting of two or more types of solvents can be used. Examples of the inert solvent can include: nitrile solvents such as acetonitrile; ether solvents such as diethyl ether, 1,2-dimethoxyethane, and tetrahydrofuran; saturated hydrocarbon solvents such as hexane and pentane; aromatic hydrocarbon solvents such as benzene, toluene, and chlorobenzene; ketone solvents such as acetone and 2-butanone; amide solvents such as N,N-dimethylformamide, N,N-dimethylacetamide, and 1-methyl-2-pyrrolidone; alcohol solvents such as methanol and ethanol; sulfoxide solvents such as dimethyl sulfoxide; ester solvents such as ethyl acetate; and water. The inert solvent is preferably an ether solvent, an aromatic hydrocarbon solvent or a nitrile solvent, and is more preferably tetrahydrofuran, toluene, or acetonitrile.

(S)-2-amino-1-propanol is used in the present step in an amount of generally 1.0 to 5.0 equivalents, preferably 1.0 to 3.0 equivalents, and more preferably 1.0 to 1.2 equivalents, with respect to the compound (3).

The reaction temperature applied in the present step is generally −50° C. to 80° C., preferably −20° C. to 50° C., and more preferably 0° C. to 30° C.

The reaction time applied in the present step is generally 1 hour to 24 hours, preferably 2 hours to 12 hours, and more preferably 3 hours to 6 hours.

Step A4

The present step is a step of adding an acid to the salts (5) of the compound in an inert solvent to remove the salts from the compound, so as to produce a compound (3). It is to be noted that a compound (4) or a pharmacologically acceptable salt thereof can be also directly produced by simultaneously performing the present step and Step A5.

The inert solvent used in the present step is generally water, or a mixture of water and an organic solvent. The organic solvent is not particularly limited, as long as it does not inhibit the reaction. Examples of the organic solvent can include: nitrile solvents such as acetonitrile; ether solvents such as diethyl ether, 1,2-dimethoxyethane, and tetrahydrofuran; saturated hydrocarbon solvents such as hexane and pentane; aromatic hydrocarbon solvents such as benzene, toluene, and chlorobenzene; ketone solvents such as acetone and 2-butanone; amide solvents such as N,N-dimethylformamide, N,N-dimethylacetamide, and 1-methyl-2-pyrrolidone; alcohol solvents such as methanol and ethanol; sulfoxide solvents such as dimethyl sulfoxide; and ester solvents such as ethyl acetate. The organic solvent is preferably a mixed solvent of an ether solvent and water or a mixed solvent of an ester solvent and water, and more preferably a mixed solvent of tetrahydrofuran and water.

The acid used in the present step is not particularly limited, as long as it generally does not inhibit the reaction. Examples of the acid can include: hydrogen halides such as hydrochloric acid; sulfonates such as p-toluenesulfonic acid and methanesulfonic acid; carboxylates such as acetic acid and trifluoroacetic acid; and sulfuric acid, phosphoric acid, and acidic cation exchange resin. The acid is preferably hydrochloric acid, p-toluenesulfonic acid or acetic acid, and is more preferably hydrochloric acid.

The acid is used in the present step in an amount of generally 1 to 5 equivalents, preferably 1 to 2 equivalents, and more preferably 1 to 1.1 equivalents, with respect to the salts (5) of the compound.

The reaction temperature applied in the present step is generally 0° C. to 100° C., preferably 10° C. to 50° C., and more preferably 20° C. to 30° C.

It is to be noted that Step A3 and Step A4 can be omitted, and that the compound (3) produced in Step A2 can be used in Step A5.

Step A5

The present step is a step of deprotecting the compound (3), so as to produce a compound (4) or a pharmacologically acceptable salt thereof. Conditions for the deprotection are not particularly limited, as long as they are generally conditions used in deprotection of protective groups for amino groups. For example, when the protective group for the amino group is a tert-butoxycarbonyl group, deprotection is carried out by adding an acid to the protective group in an inert solvent.

The inert solvent used in the present step is not particularly limited, as long as it generally does not inhibit the reaction. Examples of the inert solvent can include: nitrile solvents such as acetonitrile; ether solvents such as diethyl ether, 1,2-dimethoxyethane, and tetrahydrofuran; saturated hydrocarbon solvents such as hexane and pentane; aromatic hydrocarbon solvents such as benzene, toluene, and chlorobenzene; ketone solvents such as acetone and 2-butanone; amide solvents such as N,N-dimethylformamide, N,N-dimethylacetamide, and 1-methyl-2-pyrrolidone; alcohol solvents such as methanol and ethanol; sulfoxide solvents such as dimethyl sulfoxide; ester solvents such as ethyl acetate; and a mixed solvent of the aforementioned solvent and water. The inert solvent is preferably a mixed solvent of a ketone solvent, an ether solvent or any of these solvents, and water, and is more preferably a mixed solvent of tetrahydrofuran and water.

When the protective group for the amino group is a tert-butoxycarbonyl group, the acid used in the present step is not particularly limited, as long as it generally does not inhibit the reaction. Examples of the acid can include: hydrogen halides such as hydrochloric acid; sulfonates such as p-toluenesulfonic acid and methanesulfonic acid; carboxylates such as acetic acid and trifluoroacetic acid; and sulfuric acid and phosphoric acid. The acid is preferably hydrochloric acid, p-toluenesulfonic acid, methanesulfonic acid or trifluoroacetic acid, and is more preferably p-toluenesulfonic acid.

When the protective group for the amino group is a tert-butoxycarbonyl group, the acid is used in the present step in an amount of generally 1 to 10 equivalents, preferably 1 to 5 equivalents, and more preferably 2 to 3 equivalents, with respect to the compound (3).

When the protective group for the amino group is a tert-butoxycarbonyl group, the reaction temperature applied in the present step is generally 0° C. to 100° C., preferably 20° C. to 80° C., and more preferably 50° C. to 70° C.

When the protective group for the amino group is a tert-butoxycarbonyl group, the reaction time applied in the present step is generally 1 hour to 24 hours, preferably 2 hours to 12 hours, and more preferably 4 hours to 8 hours.

After completion of the reaction, the product generated in each of the above described steps can be isolated from the reaction mixture in the form of a free compound or a salt thereof, as necessary, according to a conventional method, for example, (1) a method of directly concentrating the reaction solution, (2) a method comprising removing insoluble matters such as a catalyst from the reaction mixture by filtration, and then concentrating the filtrate, (3) a method comprising adding water and a solvent immiscible with water (e.g., dichloromethane, diethyl ether, ethyl acetate, toluene, etc.) to the reaction solution, and then extracting the product, or (4) a method of collecting a crystallized or precipitated product by filtration. The thus isolated product can be purified, as necessary, according to an conventional method, for example, recrystallization, reprecipitation, or various types of chromatography. Otherwise, the product generated in each step can be used in the subsequent step without isolation or purification.

The compound (4) obtained by the present invention or a pharmacologically acceptable salt thereof may be present in the form of a free form or a solvate, and these solvates are also encompassed in the scope of the present invention.

Regarding the pharmacologically acceptable salt, examples of acid-addition salts formed with acids can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornitate, glutamate, and aspartate.

In addition, examples of base-addition salts formed with bases can include: alkali metal salts such as sodium salts, potassium salts, and lithium salts; alkaline-earth metal salts such as calcium salts and magnesium salts; inorganic salts such as ammonium salts; organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts, and tris(hydroxymethyl)aminomethane salts; and amino acid salts such as arginine salts.

The solvate is not particularly limited, as long as it is a pharmacologically acceptable solvate. Specifically, a hydrate, an ethanol solvate and the like are preferable, and a hydrate is more preferable. In addition, a nitrogen atom is present in the compound (4), and the nitrogen atom may be in an N-oxide form, and these solvates and N-oxide forms are also encompassed in the scope of the present invention.

EXAMPLES

Hereinafter, the present invention will be described specifically with reference to Reference Examples and Examples. However, the present invention is not limited to these methods by any means.

The symbol "$^1$H-NMR" in the Examples means a "nuclear magnetic resonance spectrum". The ratio of eluting solvents described in chromatographic separation/purification represents a volume ratio, unless otherwise specified. The terms inside the parentheses of "$^1$H-NMR" represent assay solvents, all of which used TMS (tetramethylsilane) as an internal standard. Multiplicity in $^1$H-NMR means s=singlet, d=doublet, t=triplet, q=quartet, m=multiplet, and br=broad.

Moreover, in the present specification, the following abbreviations were used:
CDCl$_3$: deuterated chloroform;
CD$_3$OD: deuterated methanol;
Boc: tert-butoxycarbonyl group;
and furthermore, the optical purity of the obtained compound was measured under the following HPLC analysis conditions.

Conditions for the measurement of the optical purity of each of (2S)-5-[(tert-butoxycarbonyl)amino]-2-{[1-(trans-4-methylcyclohexyl)-1H-imidazol-4-yl]methyl}valeric acid (S)-2-aminopropanol salts:
Column: CHIRAL AGP 4.6 mm I.D.×250 mm (5 µm),
Mobile phase: methanol/10 mM phosphate buffer (pH 7)=5/95,
Temperature: 35° C.,
Flow rate: 0.5 mL/min,
Detection method: UV at 220 nm,
Retention time: R form: 5.9 minutes, and S form: 7.3 minutes.

Example 1

(1-1) 5-[(tert-Butoxycarbonyl)amino]-2-methoxycarbonyl)valeric acid morpholine salt

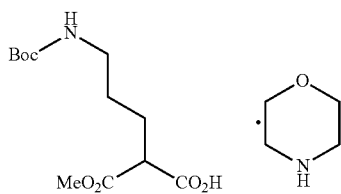

[Formula 7]

Triethylamine (51.0 g) was added dropwise to a solution of di-tert-butyl dicarbonate (100.0 g) and 3-chloropropylamine hydrochloride (71.5 g) in methanol (400 mL) at 0° C., and the mixture was then stirred at the same temperature for 16 hours. Thereafter, toluene (400 mL) and water (400 mL) were added to the reaction solution for liquid separation, and the organic layer was then washed with water. 400 mL of toluene was added to the organic layer, and the mixed solution was concentrated to 300 mL under reduced pressure. After that, N,N-dimethylacetamide (210 mL) was added, and the mixed solution was concentrated to 300 mL under reduced pressure. Thereafter, to this solution, potassium carbonate (126.66 g), tetrabutylammonium bromide (44.32 g), dimethyl malonate (90.82 g) and N,N-dimethylacetamide (100 mL) were added, and the mixed solution was then stirred at 55° C. for 20 hours. Thereafter, toluene (400 mL) and water (700 mL) were added to the reaction solution for liquid separation. The organic layer was successively washed with water, a 1 M aqueous sodium hydroxide solution and water, and was then concentrated to 150 mL under reduced pressure. To this solution, methanol (1870 mL) and a 1 M aqueous sodium hydroxide solution (430.8 mL) were added, and the mixed solution was then stirred at 0° C. for 27.5 hours. Subsequently, concentrated hydrochloric acid (2.5 mL) was added to the reaction solution, so that the pH of the solution was adjusted to pH 7-9, and the solution was then concentrated to 375 mL under reduced pressure. Ethyl acetate (500 mL) was added to the reaction solution, and concentrated hydrochloric acid (35.1 mL) was then added to the mixed solution, so that the pH of the solution was adjusted to pH 2.2-2.5, followed by liquid separation. The water layer was extracted with ethyl acetate (500 mL), the organic layer was then mixed therewith. The mixed solution was dehydrated and concentrated under reduced pressure to prepare an ethyl acetate (250 mL) solution. To the obtained solution, ethyl acetate (500 mL) and morpholine (37.5 g) were added, and the obtained mixture was stirred overnight. Thereafter, the precipitated crystals were filtrated, were then washed with ethyl acetate, and were then dried under reduced pressure to obtain the title compound (136.1 g, yield: 81.9%).

$^1$H-NMR (DMSO-d$_6$) δ: 6.79 (1H, t, J=5.5 Hz), 3.61 (4H, t, J=4.9 Hz), 3.58 (3H, s), 3.14 (1H, t, J=7.8 Hz), 2.90-2.80 (6H, m), 1.74-1.59 (2H, m), 1.37 (9H, s), 1.34-1.25 (2H, m).

(1-2) [1-(trans-4-Methylcyclohexyl)-1H-imidazol-4-yl]methanol

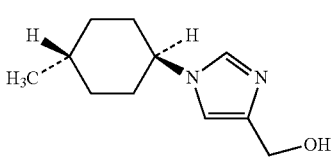

[Formula 8]

A solution of N,N-dimethylformamide dimethyl acetal (77.4 g) and isocyanoethyl acetate (70.0 g) in methanol (56 mL) was stirred at 5° C. to 10° C. for 4 hours. Thereafter, the reaction solution was cooled to 0° C., and water (5.3 mL) and trans-4-methylcyclohexylamine (105.1 g) were then added thereto. The mixture was stirred at 60° C. to 65° C. for 24 hours. Thereafter, the reaction solution was cooled to room temperature, and toluene (420 mL) and 10% saline (280 mL) and concentrated hydrochloric acid (68 mL) were then added thereto, followed by liquid separation. After that, the organic layer was washed with 10% saline (140 mL). To the organic layer, 10% saline (280 mL) and concentrated hydrochloric acid (78.4 g) were added, and the mixture was then subjected to liquid separation.

Thereafter, to the organic layer, 10% saline (210 mL) and concentrated hydrochloric acid (31.3 g) were further added, followed by liquid separation. Sodium chloride (70.0 g) was dissolved in the water layer, and toluene (420 mL) and a 50% aqueous sodium hydroxide solution (85 mL) were then added to the solution, followed by liquid separation. Thereafter, toluene (350 mL) was added to the organic layer, and the mixture was then dehydrated and concentrated under reduced pressure to prepare a toluene (420 mL) solution. This solution was cooled to 0° C., and sodium bis(2-methoxyethoxy)aluminum hydride (70% toluene solution) (207.4 g) was then added dropwise thereto. The mixture was stirred at room temperature for 1 hour. Thereafter, the reaction solution was cooled to 0° C., and a 12.5% aqueous sodium hydroxide solution (700 mL) was then added dropwise thereto. The mixture was stirred at room temperature for 1 hour. Thereafter, the solution was subjected to liquid separation, and the organic layer was successively washed with a 12.5% aqueous sodium hydroxide solution (700 mL) and 20% saline (140 mL), and then, to the organic layer, toluene (140 mL), 1-butanol (14 mL), water (280 mL) and concentrated hydrochloric acid (48 mL) were added, followed by liquid separation. Thereafter, to the organic layer, water (140 mL) and concentrated hydrochloric acid (2 mL) were further added, followed by liquid separation. The water layers were combined, activated carbon (10.5 g) was then added thereto, and the mixture was then stirred for 1 hour. Thereafter, the activated carbon was filtrated, and the filtrated activated carbon was then washed with water (210 mL). The filtrate and the washing solution were combined, and to the mixture, sodium chloride (140 g), toluene (980 mL) and a 50% aqueous sodium hydroxide solution (42 mL) were added. The obtained mixture was subjected to liquid separation, and the organic layer was then dehydrated and concentrated under reduced pressure to prepare a toluene (210 mL) solution. This solution was stirred at 50° C. to 55° C. for 30 minutes, and was then cooled to room temperature. Heptane (560 mL) was added dropwise to the solution, and the mixture was then stirred at the same temperature for 3 hours. The precipitated crystals were filtrated, and were then washed with a mixed solution of toluene/heptane (1/4). The resultant was dried under reduced pressure to obtain the title compound (77.2 g, yield: 64.2%).

$^1$H-NMR (CDCl$_3$) δ: 7.49 (1H, s), 6.91 (1H, s), 4.58 (2H, s), 3.83 (1H, tt, J=12.0, 3.9 Hz), 2.10-2.07 (2H, m), 1.87-1.84 (2H, m), 1.70-1.61 (2H, m), 1.48-1.42 (1H, m), 1.15-1.06 (2H, m), 0.95 (3H, d, J=6.5 Hz).

(1-3) Methyl (2E)-5-[(tert-butoxycarbonyl)amino]-2-{[1-trans-4-methylcyclohexyl]-1H-imidazol-4-yl}methylidene}valerate

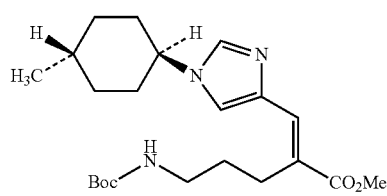

[Formula 9]

The compound (50.0 g) obtained in the above (1-2) was dissolved in a mixed solution of toluene (350 mL) and acetic acid (150 mL), and thereafter, 2,2,6,6-tetramethylpiperidine-N-oxyl (966 mg) and orthoperiodic acid (16.9 g) were added to the obtained solution at 30° C. The mixture was stirred at 30° C. to 35° C. for 1 hour. Thereafter, a 10% aqueous sodium hydrogen sulfite solution (150 mL) was added to the reaction solution, and the mixture was then stirred at room temperature for 30 minutes. After that, toluene (400 mL) was added to the reaction solution, and the mixture was then concentrated to 300 mL under reduced pressure. To this solution, toluene (400 mL) was further added, and the obtained mixture was then concentrated again to 300 mL under reduced pressure. Thereafter, toluene (500 mL), water (200 mL) and a 50% aqueous sodium hydroxide solution (118 mL) were added to the reaction solution. The mixture was subjected to liquid separation, the organic layer was then washed with 20% saline (150 mL), and toluene (200 mL) was then added thereto. The mixture was dehydrated and concentrated under reduced pressure to prepare a toluene (400 mL) solution. To this solution, the compound (116.5 g) obtained in the above (1-1), N,N-dimethylformamide (175 mL) and acetic acid (4.2 mL) were added, and the obtained mixture was then dehydrated under reflux under reduced pressure for 8 hours. Thereafter, the reaction solution was cooled to room temperature, toluene (400 mL) was then added thereto, and the obtained mixture was then washed with 5% sodium bicarbonate water (400 mL) three times, and then with 10% saline (250 mL) once. The organic layer was dehydrated and concentrated under reduced pressure to prepare a toluene (900 mL) solution. To this solution, activated carbon (15 g) was added at 35° C. to 40° C., and the mixture was then stirred at the same temperature for 30 minutes. Thereafter, the reaction solution was filtrated, and the activated carbon was washed with toluene. The filtrate and the washing solution were combined, the mixed solution was then concentrated to 250 mL under reduced pressure, and heptane (500 mL) was then added dropwise to the resulting solution at room temperature. The mixture was stirred at the same temperature for 1.5 hours, and was then cooled to 0° C. The reaction solution was stirred for 1 hour. The precipitated crystals were filtrated, were then washed with a mixed solution of toluene/heptane (1/2), and were then dried under reduced pressure to obtain the title compound (85.0 g, yield: 81.5%).

$^1$H-NMR (CDCl$_3$) δ: 7.59 (1H, s), 7.47 (1H, s), 7.15 (1H, s), 7.08 (1H, brs), 3.92-3.87 (1H, m), 3.78 (3H, s), 3.16-3.12 (2H, m), 2.96 (2H, t, J=7.5 Hz), 2.14-2.11 (2H, m), 1.90-1.87 (2H, m), 1.77-1.65 (5H, m), 1.47 (9H, s), 1.17-1.10 (2H, m), 0.96 (3H, d, J=6.5 Hz).

(1-4) (2E)-5-[(tert-Butoxycarbonyl)amino]-2-{(1-trans-4-methylcyclohexyl]-1H-imidazol-4-yl}methylidene}valeric acid

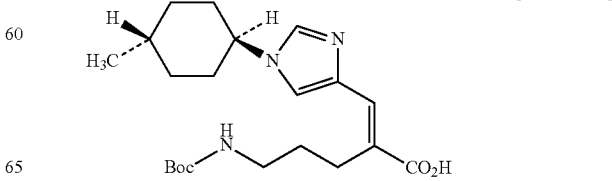

[Formula 10]

Methyl (2E)-5-[(tert-butoxycarbonyl)amino]-2-{(1-trans-4-methylcyclohexyl]-1H-imidazol-4-yl}methylidene}valerate (50.0 g) and a 7.4% aqueous sodium hydroxide solution (300 mL) were dissolved in a mixed solution of methanol (1000 mL) and tetrahydrofuran (200 mL), and this reaction solution was then stirred at room temperature for 24 hours. Thereafter, the reaction solution was concentrated to 300 mL under reduced pressure, and methanol (200 mL) and concentrated hydrochloric acid (60.78 g) were then added thereto. The mixture was stirred at room temperature for 18 hours. Thereafter, the precipitated crystals were filtrated, were then washed with a mixed solution of methanol/water (2:3), and were then dried under reduced pressure to obtain the title compound (44.87 g, yield: 93.0%).

$^1$H-NMR (CDCl$_3$) δ: 7.67 (1H, s), 7.62 (1H, s), 7.21 (1H, s), 6.77 (1H, t, J=4.9 Hz), 3.96-3.86 (1H, m), 3.20-3.13 (2H, m), 2.92 (2H, t, J=7.3 Hz), 2.18-2.07 (2H, m), 1.93-1.83 (2H, m), 1.82-1.61 (4H, m), 1.47 (9H, s), 1.18-1.09 (2H, m), 0.96 (3H, d, J=6.5 Hz).

(1-5) (2S)-5-[(tert-Butoxycarbonyl)amino]-2-{[1-(trans-4-methylcyclohexyl)-1H-imidazol-4-yl]methyl}valeric acid (S)-2-aminopropanol salt

[Formula 11]

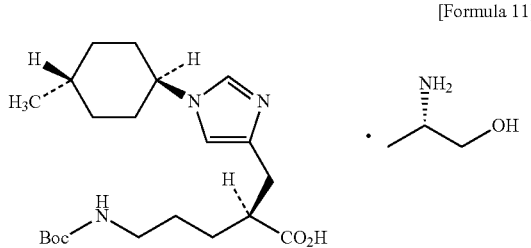

The compound (5.0 g) obtained in the above (1-4), (S)-1-[(R)-2-(di-tert-butylphosphino)ferrocenyl]-ethyl-di-2-methylphenylphosphine (manufactured by Solvias, 160.3 mg), and dichloro(benzene)ruthenium dimer (63.9 mg) were dissolved in degassed methanol (25 mL), and the mixture was then stirred under pressurized hydrogen conditions (700 kPa) at 60° C. for 40 hours. Thereafter, the reaction solution was cooled to room temperature, followed by nitrogen substitution. Thereafter, methanol (60 mL) and activated carbon (250 mg) were added to the reaction solution, and the mixture was then stirred for 15 minutes. Thereafter, the activated carbon was filtrated, the residue was washed with methanol (25 mL), and the filtrate and the washing solution were concentrated to 25 mL under reduced pressure. To this solution, toluene (50 mL) was added, and the mixture was then concentrated to 25 mL under reduced pressure. Then, toluene (50 mL) was further added to the concentrate, and the mixture was then concentrated to 25 mL under reduced pressure. This operation was repeated twice. To this solution, tetrahydrofuran (75 mL) and (S)-2-amino-1-propanol (1.2 mL) were added, and the mixture was then stirred for 4 days. The precipitated crystals were filtrated, and the crystals were washed with tetrahydrofuran and were then dried under reduced pressure to obtain the title compound (5.11 g, optical purity: 96% ee, yield: 86.2%).

$^1$H-NMR (CD$_3$OD) δ: 7.57 (1H, s), 6.94 (1H, s), 3.98-3.85 (1H, m), 3.69-3.64 (1H, m), 3.47-3.42 (1H, m), 3.29-3.23 (1H, m), 3.01 (2H, t, J=6.5 Hz), 2.84 (1H, dd, J=14.6, 8.4 Hz), 2.55 (1H, dd, J=14.6, 6.2 Hz), 2.52-2.45 (1H, m), 2.03 (2H, d, J=12.7 Hz), 1.83 (2H, d, J=13.3 Hz), 1.71 (2H, q, J=12.5 Hz), 1.60-1.44 (5H, m), 1.41 (9H, s), 1.23-1.20 (3H, m), 1.18-1.09 (2H, m), 0.94 (3H, d, J=6.8 Hz).

(1-6) (2S)-5-[(tert-Butoxycarbonyl)amino]-2-{[1-(trans-4-methylcyclohexyl)-1H-imidazol-4-yl]methyl}valeric acid

[Formula 12]

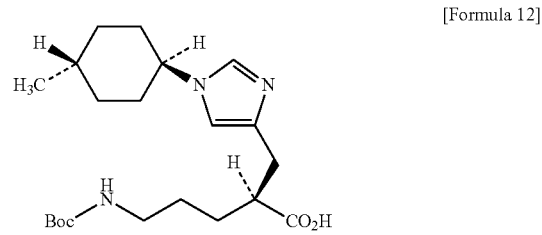 [SMILES: CC(C)(C)OC(=O)NCCC[C@@H](Cc1cn([C@H]2CC[C@H](C)CC2)cn1)C(=O)O]

The compound (40.0 g) obtained in the above (1-5) was dissolved in a mixed solvent of tetrahydrofuran (400 mL) and water (160 mL), and thereafter, concentrated hydrochloric acid (7.3 mL) and sodium chloride (40 g) were added to the obtained solution, followed by liquid separation. The organic layer was washed with 20% (w/w) saline (160 mL) three times. The organic layer was dehydrated and concentrated under reduced pressure to prepare a toluene (320 mL) solution, and tetrahydrofuran (80 mL) was then added to the solution. The mixed solution was heated to 83° C., so that the precipitated crystals were dissolved therein. The solution was cooled to room temperature, and was then stirred overnight. Thereafter, the reaction solution was further stirred at 0° C. for 3 hours, and the precipitated crystals were then filtrated. The crystals were washed with a mixed solution of toluene/tetrahydrofuran (4/1), and were then dried under reduced pressure to obtain the title compound (30.9 g, yield: 92.1%).

$^1$H-NMR (CDCl$_3$) δ: 7.59 (1H, s), 6.73 (1H, s), 4.67 (1H, brs), 3.85-3.80 (1H, m), 3.12-3.08 (2H, m), 2.88 (1H, dd, J=15.2, 8.8 Hz), 2.79 (1H, dd, J=15.2, 3.6 Hz), 2.70-2.64 (1H, m), 2.13-2.06 (2H, m), 1.90-1.82 (2H, m), 1.79-1.52 (5H, m), 1.49-1.44 (2H, m), 1.43 (9H, s), 1.15-1.05 (2H, m), 0.95 (3H, d, J=6.5 Hz).

(1-7) (2S)-5-Amino-2-{[1-(trans-4-methylcyclohexyl)-1H-imidazol-4-yl]methyl}valeric acid p-toluenesulfonate

[Formula 13]

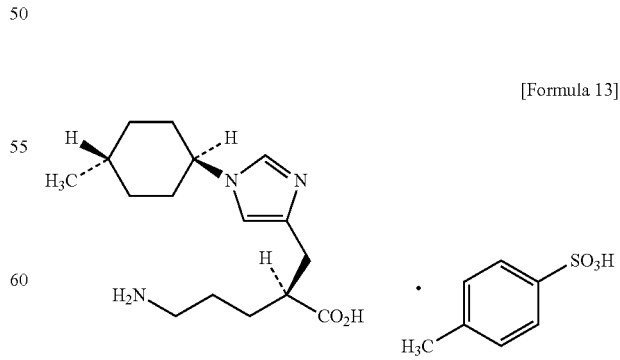

The compound (25.0 g) obtained in the above (1-6) and p-toluenesulfonic acid monohydrate (13.3 g) were dissolved in tetrahydrofuran (100 mL), and activated carbon (1.25 g)

was then added to this solution. The mixture was stirred at 20° C. to 30° C. for 1 hour. Thereafter, the activated carbon was filtrated, and the residue was washed with tetrahydrofuran (50 mL). The filtrate and the washing solution were combined, and p-toluenesulfonic acid monohydrate (13.3 g) and water (7.5 mL) were then added to the obtained solution. The obtained mixture was heated to reflux for 6 hours. The reaction solution was cooled to room temperature, and triethylamine (7.7 g) was then added thereto. The mixture was stirred at room temperature overnight. Thereafter, tetrahydrofuran (350 mL) was added dropwise to the reaction solution, the mixture was then stirred at room temperature for 3 hours, and the precipitated crystals were then filtrated. The resultant was washed with a mixed solution of tetrahydrofuran/water (50/1), and was then dried under reduced pressure to obtain the title compound (27.7 g, yield: 93.5%).

$^1$H-NMR (CD$_3$OD) δ: 8.18 (1H, s), 7.70 (2H, d, J=8.1 Hz), 7.22 (2H, d, J=7.5 Hz), 7.16 (1H, s), 4.06 (1H, tt, J=12.0, 3.9 Hz), 2.94-2.86 (3H, m), 2.69 (1H, dd, J=14.6, 5.8 Hz), 2.62-2.59 (1H, m), 2.36 (3H, s), 2.08-2.05 (2H, m), 1.86-1.83 (2H, m), 1.76-1.46 (7H, m), 1.18-1.11 (2H, m), 0.94 (3H, d, J=6.5 Hz).

Example 2

(2-1) Methyl (2S)-5-[(tert-butoxycarbonyl)amino]-2-{[1-(trans-4-methylcyclohexyl)-1H-imidazol-4-yl]methyl}valerate

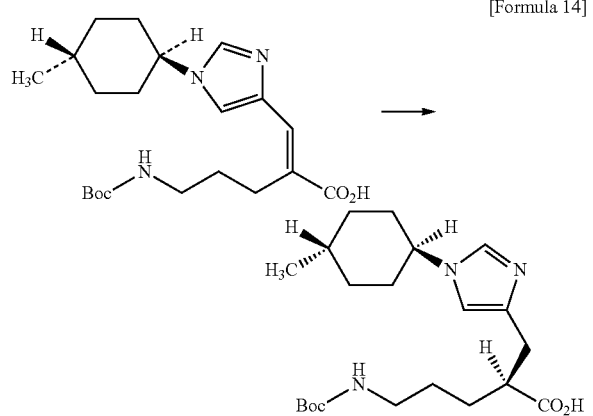

[Formula 14]

Using several catalysts, asymmetric reduction was carried out. The reaction conversion rate and optical purity of the obtained title compound were measured under the following HPLC analysis conditions.

Measurement of Reaction Conversion Rate:
  Column: Waters XBridge C18 4.6 mm I.D.×150 mm (3.5 μm),
  Mobile phase: (A) 10 mM aqueous ammonium acetate solution, (B) acetonitrile,
  Gradient conditions: B: conc.; 20% (0-5 min), 20%-90% (5-20 min), 90% (20-24 min),
  Temperature: 40° C.,
  Flow rate: 1.0 mL/min,
  Detection method: UV at 215 nm
  Retention time: raw material: 15.8 minutes, product: 13.7 minutes, Reaction conversion rate=peak area of product/(peak area of raw material+peak area of product).

Conditions for measurement of optical purity:
  Column: CHIRALAGP 4.6 mm I.D.×250 mm (5 μm),
  Mobile phase: methanol/10 mM phosphate buffer (pH 7)=5/95,
  Temperature: 35° C.,
  Flow rate: 0.5 mL/min,
  Detection method: UV at 220 nm,
  Retention time: R form: 5.9 minutes, and S form: 7.3 minutes.

(i) Asymmetric reduction using (S)-1-[(R)-2-(di-tert-butylphosphino)ferrocenyl]-ethyl-di-2-methylphenylphosphine and [RuCl$_2$(benzene)]$_2$

[(tert-Butoxycarbonyl)amino]-2-{[1-(trans-4-methylcyclohexyl)-1H-imidazol-4-yl]methylidene}valeric acid (50.0 mg), (S)-1-[(R)-2-(di-tert-butylphosphino)ferrocenyl]-ethyl-di-2-methylphenylphosphine (2.40 mg), and dichloro(benzene)ruthenium(II) (dimer) (0.96 mg) were added to an autoclave container, and nitrogen substitution was then carried out. Thereafter, vacuum-degassed methanol (0.5 mL) was added to the autoclave container under the nitrogen atmosphere. The nitrogen atmosphere in the container was substituted with hydrogen, and the pressure was increased to 600-800 kPa by hydrogen addition. The temperature was increased to 60° C., and the mixture was then stirred for 42 hours. Thereafter, the reaction solution was cooled to room temperature, and the resulting product was then analyzed by HPLC, so as to obtain the reaction conversion rate and the optical purity (reaction conversion rate: 100%, optical purity: 91.5% ee).

(ii) Asymmetric reduction using (αS,αS)-2,2'-bis(α-N,N-dimethylaminophenylmethyl)-(R,R)-1,1'-bis[di-(3,5-dimethyl-4-methoxyphenyl)-phosphino]-ferrocene and [RuCl$_2$(benzene)]$_2$

[(tert-Butoxycarbonyl)amino]-2-{[1-(trans-4-methylcyclohexyl)-1H-imidazol-4-yl]methylidene}valeric acid (50.0 mg), (αS,αS)-2,2'-bis(α-N,N-dimethylaminophenylmethyl)-(R,R)-1,1'-bis[di-(3,5-dimethyl-4-methoxyphenyl)-phosphino]-ferrocene (4.44 mg), and dichloro(benzene)ruthenium(II) (dimer) (0.96 mg) were added to an autoclave container, and nitrogen substitution was then carried out. Thereafter, vacuum-degassed methanol (0.5 mL) was added to the autoclave container under the nitrogen atmosphere. The nitrogen atmosphere in the container was substituted with hydrogen, and the pressure was increased to 600-800 kPa by hydrogen addition. The temperature was increased to 60° C., and the mixture was then stirred for 42 hours. Thereafter, the reaction solution was cooled to room temperature, and the resulting product was then analyzed by HPLC, so as to obtain the reaction conversion rate and the optical purity (reaction conversion rate: 100%, optical purity: 88.6% ee).

(iii) Asymmetric reduction using (αS,αS)-2,2'-bis(α-N,N-dimethylaminophenylmethyl)-(R,R)-1,1'-bis[di-(3,5-dimethylphenyl)phosphino]-ferrocene and [RuCl$_2$(benzene)]$_2$

[(tert-Butoxycarbonyl)amino]-2-{[1-(trans-4-methylcyclohexyl)-1H-imidazol-4-yl]methylidene}valeric acid (50.0 mg), (αS,αS)-2,2'-bis(α-N,N-dimethylaminophenylmethyl)-(R,R)-1,1'-bis[di-(3,5-dimethylphenyl)phosphino]-ferrocene (3.93 mg), and dichloro(benzene)ruthenium(II) (dimer) (0.96 mg) were added to an autoclave container, and nitrogen substitution was then carried out. Thereafter, vacuum-degassed methanol (0.5 mL) was added to the autoclave container under the nitrogen atmosphere. The nitrogen atmosphere in the container was substituted with hydrogen, and the pressure was increased to 600-800 kPa by hydrogen addition. The temperature was increased to 60° C., and the mixture was then stirred for 42 hours. Thereafter, the reaction solution was cooled to room temperature, and the resulting product was then analyzed by HPLC, so as to obtain the reaction conversion rate and the optical purity (reaction conversion rate: 100%, optical purity: 89.2% ee).

INDUSTRIAL APPLICABILITY

According to the present invention, an optically active valeric acid derivative substituted with a cycloalkyl group, which has an excellent TAFIa inhibitory activity, can be efficiently produced by simple operations.

The invention claimed is:
1. A method of producing a compound of formula (3):

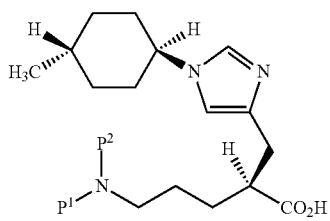

comprising allowing a compound of formula (1):

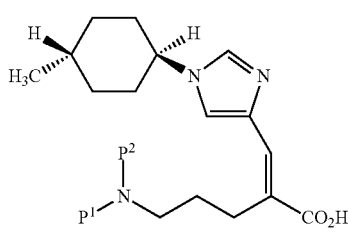

to react with hydrogen gas, in an inert solvent, in the presence of a chiral ligand of formula (2):

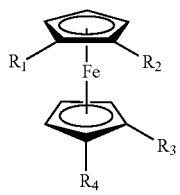

and a ruthenium catalyst, or in the presence of an asymmetric transition metal complex catalyst previously generated from the chiral ligand and the ruthenium catalyst,
wherein $P^1$ and $P^2$ are each independently a hydrogen atom or a protective group for the amino group,
$R^1$ is an (S)-ethyl-di-2-methylphenylphosphino group or an (S)-α-N,N-dimethylaminophenylmethyl group,
$R^2$ is a di-tert-butylphosphino group, a di(3,5-dimethyl-4-methoxyphenyl)-phosphino group, or a di(3,5-dimethylphenyl)-phosphino group,
$R^3$ is an (S)-α-N,N-dimethylaminophenylmethyl group or a hydrogen atom, and
$R^4$ is a di(3,5-dimethyl-4-methoxyphenyl)-phosphino group, a di(3,5-dimethylphenyl)-phosphino group, or a hydrogen atom.

2. The method of claim 1, wherein at least one of $P^1$ and $P^2$ is a tert-butoxycarbonyl group, a methoxycarbonyl group, an ethoxycarbonyl group, a 2,2,2-trichloroethoxycarbonyl group, a 2-trimethylsilylethoxycarbonyl group, an allyloxycarbonyl group, a benzyloxycarbonyl group, a 4-methoxybenzyloxycarbonyl group, a 4-nitrobenzyloxycarbonyl group, a 2-nitrobenzyloxycarbonyl group, a 9-fluorenylmethyloxycarbonyl group, a benzyl group, a 4-methoxybenzyl group, a 2,3-dimethoxybenzyl group, a 3,4-dimethoxybenzyl group, a diphenylmethyl group, a triphenylmethyl group, a formyl group, an acetyl group, a trimethylacetyl group, a trichloroacetyl group, a trifluoroacetyl group, a benzoyl group, a benzenesulfonyl group, a p-toluenesulfonyl group, a 2-nitrobenzenesulfonyl group, a 4-nitrobenzenesulfonyl group, or a 2,4-dinitrobenzenesulfonyl group.

3. The method of claim 1, wherein at least one of $P^1$ and $P^2$ is a tert-butoxycarbonyl group.

4. The method of claim 1, wherein one of $P^1$ and $P^2$ is a tert-butoxycarbonyl group and the other is a hydrogen atom.

5. The method of claim 1, wherein the chiral ligand is (S)-1-[(R)-2-(di-tert-butylphosphino)ferrocenyl]-ethyl-di-2-methylphenylphosphine, (αS,α(S)-2,2'-bis(α-N,N-dimethylaminophenylmethyl)-(R,R)-1,1'-bis[di-(3,5-dimethyl-4-methoxyphenyl)-phosphino]-ferrocene, or (αS,αS)-2,2'-bis(α-N,N-dimethylaminophenylmethyl)-(R,R)-1,1'-bis[di-(3,5-dimethylphenyl)phosphino]-ferrocene.

6. The method of claim 1, wherein the chiral ligand and the ruthenium catalyst are, respectively, (S)-1-[(R)-2-(di-tert-butylphosphino)ferrocenyl]-ethyl-di-2-methylphenylphosphine and [RuCl$_2$(benzene)]$_2$, (αS,αS)-2,2'-bis(α-N,N-dimethylaminophenylmethyl)-(R,R)-1,1'-bis[di-(3,5-dimethyl-4-methoxyphenyl)-phosphino]-ferrocene and [RuCl$_2$(benzene)]$_2$, or (αS,αS)-2,2'-bis(α-N,N-dimethylaminophenylmethyl)-(R,R)-1,1'-bis[di-(3,5-dimethylphenyl)phosphino]-ferrocene and [RuCl$_2$(benzene)]$_2$.

7. The method of claim 1, wherein the chiral ligand and the ruthenium catalyst are (S)-1-[(R)-2-(di-tert-butylphosphino)ferrocenyl]-ethyl-di-2-methylphenylphosphine and [RuCl$_2$(benzene)]$_2$, respectively.

8. The method of claim 1, wherein the inert solvent is an alcohol.

9. The method of claim 1, wherein the inert solvent is methanol.

10. A method of producing a compound of formula (4):

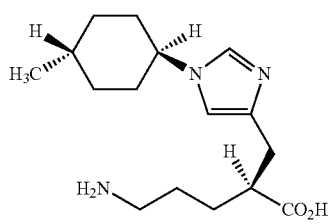

or a pharmacologically acceptable salt thereof,
comprising producing the compound of the formula (3) by the method of claim 1, and
deprotecting the protective group(s) for the amino group of the compound of formula (3).

11. A method of producing a compound of formula (4):

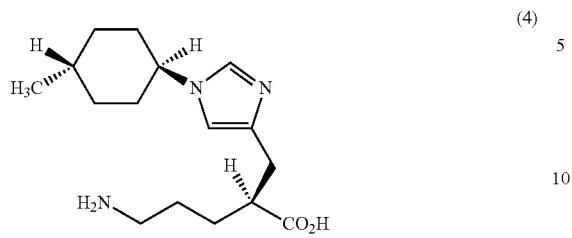

(4)

or a pharmacologically acceptable salt thereof,
comprising producing the compound of formula (3) by the method of claim 1, and
performing the following steps on the compound of formula (3):
adding (S)-2-amino-1-propanol to crystallize a salt of the compound, then,
adding an acid to remove the salt from the compound, and then,
deprotecting the protective group(s) for the amino group.

* * * * *